(12) United States Patent
Vogt et al.

(10) Patent No.: US 9,593,578 B2
(45) Date of Patent: Mar. 14, 2017

(54) COMPRESSED GAS MOTOR AND LAVAGE SYSTEM

(75) Inventors: Sebastian Vogt, Erfurt (DE); Hubert Buechner, Nuremberg (DE)

(73) Assignee: Heraeus Medical GmbH, Wehrheim (DE)

(*) Notice: Subject to any disclaimer, the term of this patent is extended or adjusted under 35 U.S.C. 154(b) by 1028 days.

(21) Appl. No.: 13/823,802

(22) PCT Filed: Aug. 10, 2011

(86) PCT No.: PCT/EP2011/003993
§ 371 (c)(1),
(2), (4) Date: Mar. 15, 2013

(87) PCT Pub. No.: WO2012/038003
PCT Pub. Date: Mar. 29, 2012

(65) Prior Publication Data
US 2013/0180396 A1 Jul. 18, 2013

(30) Foreign Application Priority Data
Sep. 22, 2010 (DE) .......... 10 2010 046 057

(51) Int. Cl.
*F01B 1/00* (2006.01)
*A61M 1/00* (2006.01)
(Continued)

(52) U.S. Cl.
CPC .............. *F01B 1/00* (2013.01); *A61M 1/0064* (2013.01); *A61M 1/0068* (2014.02); *F01B 11/007* (2013.01); *F01B 17/02* (2013.01)

(58) Field of Classification Search
CPC F01B 1/00; F01B 17/02; F01B 11/007; F04B 9/135; F04B 53/143; A61M 1/0068;
(Continued)

(56) References Cited

U.S. PATENT DOCUMENTS 3,912,168 A * 10/1975 Mullins ............... A61M 3/0275
239/101
4,278,078 A 7/1981 Smith
(Continued)

FOREIGN PATENT DOCUMENTS

EP 0 378 434 A2 7/1990
EP 0 481 208 A1 4/1992
(Continued)

OTHER PUBLICATIONS

Breusch, et al., "Zementierte Hüftendoprothetik—Verminderung des Fettembolierisikos mittels gepulster Druckspülung"; Orthopädie, 2000, vol. 29, pp. 578-586, Heidelberg, Germany. English Abstract on p. 579.
(Continued)

*Primary Examiner* — Manuel Mendez
(74) *Attorney, Agent, or Firm* — Norris McLaughlin & Marcus, P.A.

(57) ABSTRACT

A compressed-gas motor has a cylindrical inner chamber closed gas-tight at a first base surface, and a piston arranged so as to be movable along the cylinder axis in the cylindrical inner chamber. A first opening feeds a compressed gas into the inner chamber, and a second opening discharges a gas from inside the inner chamber. The openings are arranged in the cylinder casing of the cylindrical inner chamber, wherein the first opening is arranged between the second opening and the closed first base surface. The first opening is closable by a first piston part and the second opening by a second piston part. The compressed-gas motor has a resetting device which exerts a force on the piston in the direction of the first base surface of the cylindrical inner chamber if the second piston part does not completely close the second opening.

23 Claims, 4 Drawing Sheets

Figure 1:
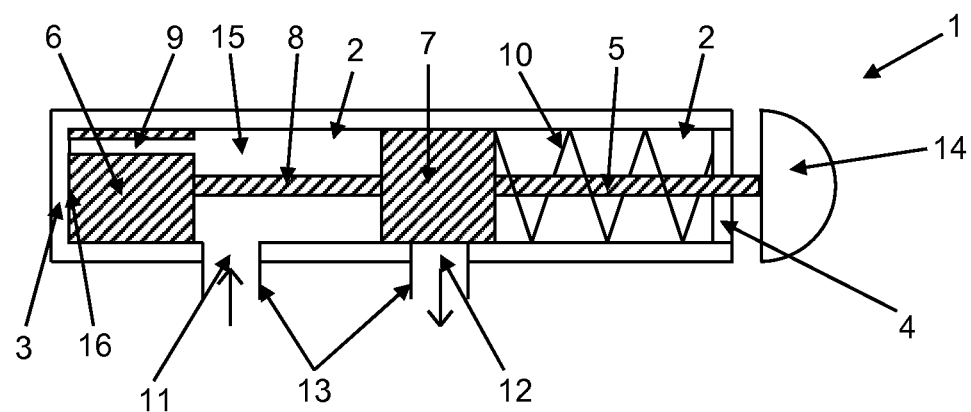

(51) Int. Cl.
*F01B 11/00* (2006.01)
*F01B 17/02* (2006.01)

(58) Field of Classification Search
CPC . A61M 1/0064; A61M 3/0258; A61M 3/0254
USPC ........ 604/146, 143, 141, 140, 73, 35, 30, 27
See application file for complete search history.

(56) References Cited

U.S. PATENT DOCUMENTS

| | | | |
|---|---|---|---|
| 4,583,531 A | | 4/1986 | Mattchen |
| 5,542,918 A | * | 8/1996 | Atkinson ............ A61M 1/0064 417/401 |
| 2002/0176788 A1 | * | 11/2002 | Moutafis ............... F04B 53/143 417/415 |
| 2005/0084395 A1 | * | 4/2005 | Kang ...................... F04B 9/135 417/392 |
| 2015/0308421 A1 | * | 10/2015 | Vogt .................... A61M 3/0258 604/146 |

FOREIGN PATENT DOCUMENTS

| | | |
|---|---|---|
| JP | 2002 061566 A | 2/2002 |
| WO | WO 96/00524 A1 | 1/1996 |

OTHER PUBLICATIONS

Breusch, et al., "Lavage Technique in Total Hip Arthroplasty, Jet Lavage Produces Better Cement Penetration Than Syringe-Lavage in the Proximal Femur"; The Journal of Arthroplasty; 2000, pp. 921-927, vol. 15, No. 7; Churchill Livingstone; Heidelberg, Germany.

Byrick, et al., "High-volume, High-Pressure Pulsatile Lavage During Cemented Arthroplasty," The Journal of Bone and Joint Bone Joint Surgery, Incorporated; 1989, pp. 1331-1336, Canada.

Christie, et al., "Medullary Lavage Reduces Embolic Phenomena and Cardiopulmonary Changes During Cemented Hemiarthroplasty," British Editorial Society of Bone and Joint Surgery; 1995, vol. 77-B, pp. 456-459, United Kingdom.

Sherman, et al., "The Role of Lavage in Preventing Hemodynamic and Blood-Gas Changes During Cemented Arthroplasty," The Journal of Bone and Joint Surgery, Incorporated; 1983, vol. 65-A, pp. 500-506, Canada.

Chinese Office Action for corresponding Chinese Patent Application No. 201180045522.8 dated Nov. 26, 2014.

International Search Report and Written Opinion for PCT Application No. PCT/EP2011/003993 dated Mar. 22, 2013.

* cited by examiner

COMPRESSED GAS MOTOR AND LAVAGE SYSTEM

This is a 371 of PCT/EP2011/003993 filed 10 Aug. 2011 (international filing date), and claims the priority of German Application No. 10 2010 046 057.5 filed 22 Sep. 2010.

The invention relates to a compressed gas motor for operating a lavage system, comprising a cylindrical internal space that is closed in gas-tight manner at least at one first base surface, at least one plunger that is arranged in the cylindrical internal space such as to be mobile along the cylinder axis and ends tightly against the internal space, a plunger rod that is connected to the plunger and projects from the internal space beyond the second base surface, a first opening for supplying a compressed gas into the internal space, and a second opening for discharging a gas from the inside of the internal space.

The invention also relates to a handle for a lavage system having a compressed gas motor of this type as well as a lavage system having a compressed gas motor of this type, and a method for operating a compressed gas motor of this type.

Accordingly, the subject matter of the invention is a simple driving device for generating oscillating linear motions through the use of compressed gas as driving means for a lavage system. Moreover, a handle for a lavage system having the driving device is a subject matter of the invention. A lavage system having the driving device and a handle is also subject matter of the invention.

Lavage systems are used widely in surgery to clean tissue areas. Specifically during the implantation of articular endoprostheses and during septic revisions, lavage systems have essential significance (R. M. Sherman et al.: The role of lavage in preventing hemodynamic and blood-gas changes during cemented arthroplasty. J. Bone Joint. Surg. 1983; 65-A: 500-506; S. J. Breusch et al.: Zementierte Hüftendoprothetik: Verminderung des Fettembolierisikos in der zementierten Hüftendoprothetik mittels gepulster Druckspülung. Orthopädie 2000; 29: 578-586; S. J. Breusch et al.: Lavage technique in THA: Jet-lavage Produces Better Cement Penetration Than Syringe-Lavage in the Proximal Femur. J. Arthroplasty. 200; 15(7): 921-927; R. J. Byrick et al.: High-volume, high pressure pulsatile lavage during cemented arthroplasty. J. Bone Joint Surg. 1989; 81-A: 1331-1336; J. Christie et al.: Medullary lavage reduces embolic phenomena and cardiopulmonary changes during cemented hemiarthroplasty. J. Bone Joint Surg. 1995; 77-B: 456-459.) Tissue areas are cleaned during lavage by means of spray puffs of suitable rinsing liquids, such as isotonic saline solutions. Up to several thousand spray puffs per minute are common in this context.

Pulsed lavage systems have been known for a long time, for example from U.S. Pat. No. 4,583,531 A, U.S. Pat. No. 4,278,078 A, and U.S. Pat. No. 5,542,918 A. The lavage systems currently on the market are driven by means of electrical motors (for example InterPulse® Jet lavage of Stryker GmbH & Co. KG) or compressed air (for example PALAVAGE® of Heraeus Medical GmbH).

Battery-operated lavage systems, for example, have proven useful. However, a large battery block, which only has a limited charge capacity due to its nature, always needs to be taken along. Compressed air-driven lavage systems are advantageous by comparison in that compressed air is available in the operating theatre in unlimited quantities and thus allows rinsing liquid to be sprayed for any desired time without the energy supply being limited.

Systems driven by compressed air or other compressed gases usually utilise a compressed gas motor as the drive. Most compressed gas motors for lavage systems are lamellar compressed gas motors. The compressed gas motor generates a rotary motion which is then converted into an oscillating linear motion. The oscillating linear motion is utilised to convey momentum to small volumes of a rinsing medium. It is common in this context to arrange at least one membrane between the drive and the inlet of rinsing liquid in order to be able to transmit the pulses to the rinsing liquid. This generates spray puffs. At high pulse rates of 2,000 to 3,000 pulses per minute, volumes in the range of several hundred milliliters of rinsing liquid are sprayed. This means that the compressed gas motor needs to be manufactured at high precision in order to tolerate such high rotation rates. Moreover, sufficiently stable storage must be available. For these reasons, the compressed gas motor is the most expensive component of common compressed air-driven lavage systems. Therefore, the compressed gas motor is generally arranged in a handle made of metal or other durable materials such that this component can be used multiply after appropriate reprocessing and sterilisation.

A generic compressed gas motor is known from EP 0 481 208 A1 and has pneumatically driven pinch valves that are arranged laterally next to a plunger that is mobile in linear direction in a cylindrical hollow space. In this design, the pinch valves control the driving compressed air driving the plunger. The plunger has compressed air applied in alternating manner to its two sides in order to elicit a linear oscillating motion of the plunger.

This is disadvantageous in that the design of the pinch valves is relatively complicated which makes them laborious to assemble. A design of this type can therefore not be implemented inexpensively.

The invention is based on the object to overcome the disadvantages of the prior art, in particular to provide a simple compressed gas motor for a lavage system that consist of the least number of parts possible and can be driven through compressed gas. Said driving device should mostly consist of inexpensive components. This should enable provision of a driving device for single use at low manufacturing and assembly costs. Expensive parts requiring precise, stable storage should be avoided as much as possible.

The object of the invention is met in that the openings are arranged in the cylinder jacket of the cylindrical internal space, whereby the first opening is arranged between the second opening and the closed first base surface, the plunger comprises a first plunger part and a second plunger part that are connected to each other, whereby the first plunger part comprises at least one passage and/or forms at least one passage between the first plunger part and the cylinder wall of the internal space and the second plunger part closes the inside of the internal space such as to be tight, whereby at least one passage of the first plunger part connects an intermediate space between the first and the second plunger part to an internal space region between the closed first base surface and the first plunger part, and whereby the first opening can be closed through the first plunger part and the second opening can be closed through the second plunger part, and the compressed gas motor comprises a restoring facility that exerts, at least for part of the time, a force on the plunger in the direction of the first base surface of the cylindrical internal space when the second plunger part does not close the second opening completely.

A hollow cylinder in the scope of the invention refers to the internal hollow cylinder. As is common for any motor in general, the part, in which the cylinder is provided, for example the motor block, does not need to have cylindrical symmetry. Moreover, a hollow cylinder in the scope of the invention shall be understood not only to be a body with a simple cylindrical geometry, but the term rather also includes hollow cylinders with non-circular, for example rectangular or even irregularly shaped base surface. The hollow cylinder needs to have a constant cross-sectional shape perpendicular to the cylinder axis in the region, in which the plungers move, i.e. be a cylinder in its most general shape.

According to the invention, the intermediate space has a constant volume, whereas the volume of the internal space region depends on the position of the plunger parts relative to the internal space.

The invention can just as well provide the wall of the internal space to comprise a groove that extends from the region of the end of the first base surface of the internal space to the region of the height of the second opening and which forms at least one passage between the first plunger part and the cylinder wall of the internal space, whereby the groove is not connected to the openings.

In turn, the invention can provide in this context that the groove extends up to the end of the first base surface of the cylindrical internal space and that the first plunger part preferably is a cylindrical body which particularly preferably comprises no further passages.

Compressed gas motors according to the invention can also be characterised in that the first plunger part and the second plunger part are connected to each other by means of a rigid connection, preferably by means of a rod, particularly preferably by means of an extension of the plunger rod, in particular along the cylinder axis.

The invention can just as well provide the second base surface of the cylindrical internal space to be open.

Moreover, the invention can provide a bracket for the plunger rod to be arranged on the second base surface of the cylindrical internal space and to support the plunger rod like in a bearing preferably centric in the region of the cylinder axis of the internal space.

The invention can just as well provide the at least one passage to comprise a patent, gas-permeable bore hole in the first plunger part, in particular provides it to be a bore hole of this type.

Another refinement of the invention provides the distance between the first plunger part and the second plunger part to be more than 1 mm, preferably between 1 mm and 100 mm, and particularly preferably between 5 mm and 10 mm.

The invention can just as well provide the distance of the first opening from the closed first base surface to be at least equal to the height of the first plunger part in the direction of the cylinder axis of the internal space.

Compressed gas motors according to the invention can also be characterised in that the first plunger part and/or the second plunger part are cylindrical, at least regions thereof, and touch tightly against the internal wall of the cylindrical internal space.

The invention can provide a reservoir to be connected at the first opening and to contain a compressed gas and/or the second opening to be connected to the surroundings of the compressed gas motor in gas-permeable manner, preferably without any conduits impeding the gas flow.

Moreover, the invention can provide attaching means, in particular a bayonet catch, for attachment of a lavage attachment to be arranged on the outside in the region of the second base surface.

It can be advantageous for the end of the plunger rod projecting from the second base surface to comprise a pestle, in particular a mushroom-shaped pestle.

Compressed gas motors according to the invention are particularly cost-efficient if the plunger parts, the connections of the plunger parts, the plunger rod, the walls of the cylindrical internal space, the end(s) of the base surfaces, the bracket, the restoring facility, the attaching means and/or the pestle are made of plastic material, in particularly if these are injection moulding components.

The invention can just as well provide the internal space to be the inside of a cylindrical tube and the compressed gas motor to comprise, at least in regions thereof, preferably essentially, a cylindrical external surface.

Particularly advantageously, the invention provides for an oscillating motion of the plunger in the internal space, that the first opening and the second opening can be closed completely through the first plunger part and the second plunger part, respectively, in alternating manner.

The invention can provide the restoring facility to comprise a spring, in particular a plastic spring, steel spring and/or gas spring that is arranged between the second plunger part and the second base surface of the cylindrical internal space.

Alternatively, the invention can provide the restoring facility to comprise a third plunger part, a third opening for discharge of a gas from the inside of the internal space, and a fourth opening for supplying a compressed gas into the internal space, whereby the third and fourth openings are arranged in the cylinder jacket of the cylindrical internal space, the fourth opening is arranged between the second opening and the second base surface of the cylindrical internal space, the third opening is arranged between the second opening and the fourth opening, the third opening and the fourth opening can be closed through the second plunger part and the third plunger part, respectively, and whereby the third plunger part is a part of the plunger that is arranged on the plunger rod between the second plunger part and the second base surface of the cylindrical internal space and is connected to the second plunger part, and the third plunger part comprises at least one passage and/or forms at least one passage between the third plunger part and the cylinder wall of the internal space.

In this context, the invention can provide the third plunger part to be structured like a first plunger part of this type and/or the internal wall of the internal space to be structured with respect to the third plunger part like it is structured with respect to the first plunger part.

Compressed gas motors according to the invention can also be provided to have the plunger rod connected to the plunger such as to be rigid and immobile, preferably to be connected to the second plunger part or the third plunger part, in particular in the region of the cylinder axis.

The object of the invention is also met by a handle for a lavage system comprising said compressed gas motor, comprising a valve and an operating facility for controlling the valve that is arranged on the handle, whereby the valve is arranged in a conduit, in particular in a compressed gas conduit that is connected to the first opening and/or second opening, preferably to the first, and particularly preferably to the first and fourth openings.

The object of the invention is also met by a lavage system comprising said compressed gas motor, preferably comprising said handle, moreover comprising a rinsing liquid reservoir and/or a connector for a rinsing liquid reservoir, whereby impacts of force can be transmitted by means of the end of the plunger rod that projects beyond the second base surface, in particular by means of the pestle, to a force transmission facility, preferably a membrane, in order to generate spray puffs containing the rinsing liquid.

And lastly, the object is met by a method for operating said compressed gas motor comprising the following steps: supplying a compressed gas through the first opening into an intermediate space between the first and second plunger part;
building-up a positive pressure in the intermediate space; motion of the plunger parts in the internal space of the compressed gas motor due to the positive pressure;
closing the first opening and opening the second opening through the motion of the plunger parts;
releasing the expanded gas through the second opening from the intermediate space;
restoring the plunger parts in the internal space through a restoring facility.

Sealing means, such as O-rings, are also all but dispensable in a structure according to the invention.

The invention is therefore based on the surprising finding that simple means allow a linearly oscillating compressed air plunger motor and/or linear compressed gas plunger motor to be built-up in that a plunger is made up of at least two plunger parts and a connection that should be as rigid as possible. A non-rigid connection would worsen the performance of the motor, but would not fully preclude the functional principle and might even result in some positive properties for a stable run of the compressed gas motor. If the motor is not desired to be durable for a long period of time, a compressed gas motor of this type can be manufactured easily from inexpensive components such that a lavage system having a compressed gas motor of this type can be designed as a disposable product.

Accordingly, driving devices according to the invention for a lavage system can be characterised in that
a) a hollow cylinder is arranged;
b) the hollow cylinder is closed on one end in gas-tight manner;
c) the hollow cylinder has an open cylinder end;
d) a rod is present in the cylinder;
e) one end of the rod has a first plunger part arranged on it that possesses at least one patent gas-permeable bore hole in axial direction and is fixedly connected to the rod;
f) a second plunger part is arranged on the rod next to the first plunger part, whereby the second plunger part contains no gas passages and is fixedly connected to the rod;
g) a distance of at least 1.0 mm is present between the first plunger part and the second plunger part;
h) the second plunger part contacts a spring on its side facing away from the first plunger part, which spring is supported through a plate that is permeable to the rod or through a fin;
i) a first opening has a distance from the closed end of the hollow cylinder that is at least equal to the length of the first plunger part;
j) the length of the spring is such that the first plunger part is pressed against the closed end of the hollow cylinder such that the first opening is not covered by the first plunger part, and the second plunger part covers a second opening;
k) the first plunger part and the second plunger part touch tightly against the internal wall of the hollow cylinder;
l) the first opening is connected to a reservoir containing a compressed gas; and
m) the second opening is connected to the surroundings in gas-permeable manner, whereby the pressure in the surroundings is lower than the compressed gas pressure in the reservoir.

Devices according to the invention function, for example, in that a restoring facility, such as a spring, presses the first and second plunger parts of the plunger rod against the closed end of the hollow cylinder. In this context, the first opening is open and the second opening is covered and thus closed through the second plunger part. When compressed gas is guided through the first opening into the cylindrical internal space, the compressed gas enters into the intermediate space between the first and second plunger parts. The gas then moves through the at least one gas-permeable passage in the first plunger part until it reaches the closed gas-tight end of the internal space. The gas expands and pushes the two plunger parts in the direction of the end of the internal space through which the plunger rod extends. In this context, the first plunger part moves until the first opening becomes covered through the first plunger part. The second plunger part moves synchronously and opens up the second opening. If a low ambient pressure is applied to the second opening, the compressed gas escapes from the region between the two plungers and the region between the first plunger part and the end of the closed internal space through the at least one gas-permeable passage in the first plunger part. The internal pressure in the internal space is then equal to the external pressure. The restoring element then presses onto the second plunger part and moves it together with the plunger rod and the first and second plunger part back into the starting position. Then the cycle starts anew.

Figure 2:
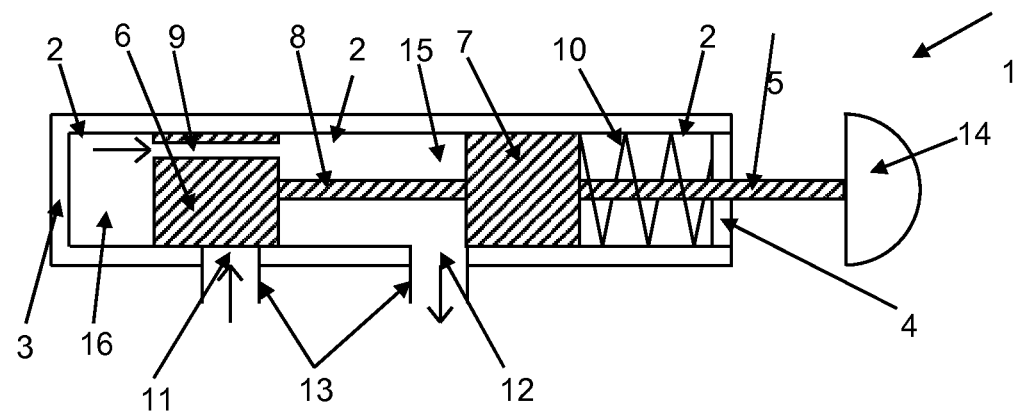
Figure 3:
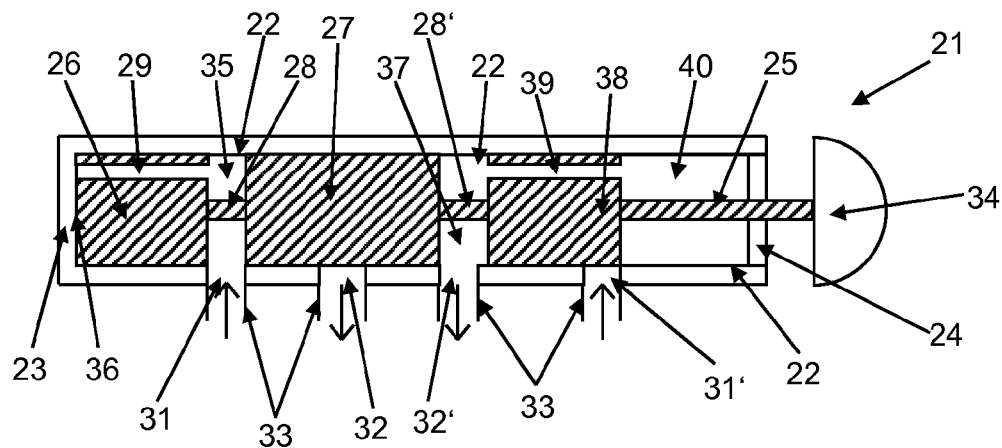
Figure 4:
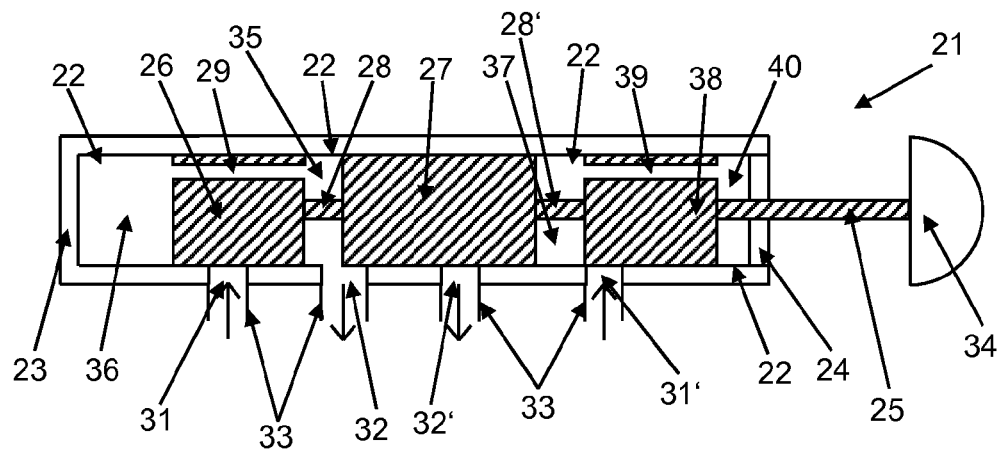
Figure 5:
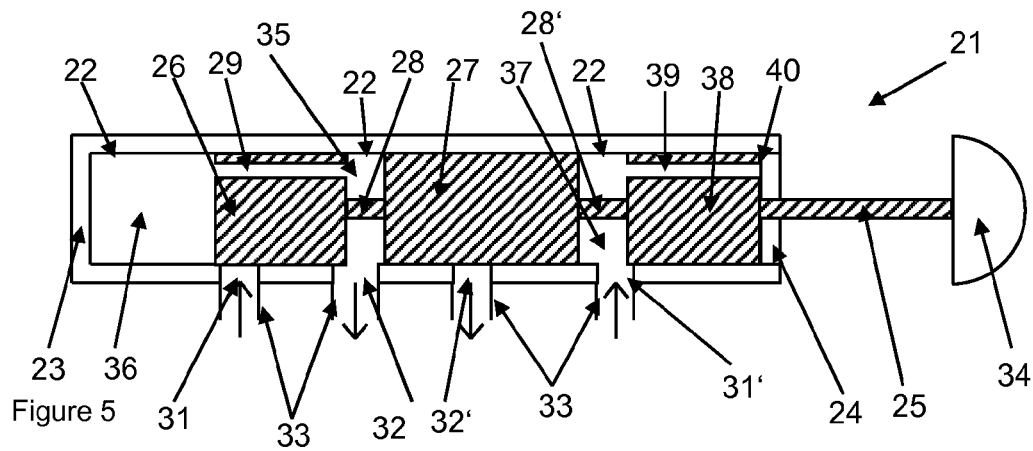
Figure 6:
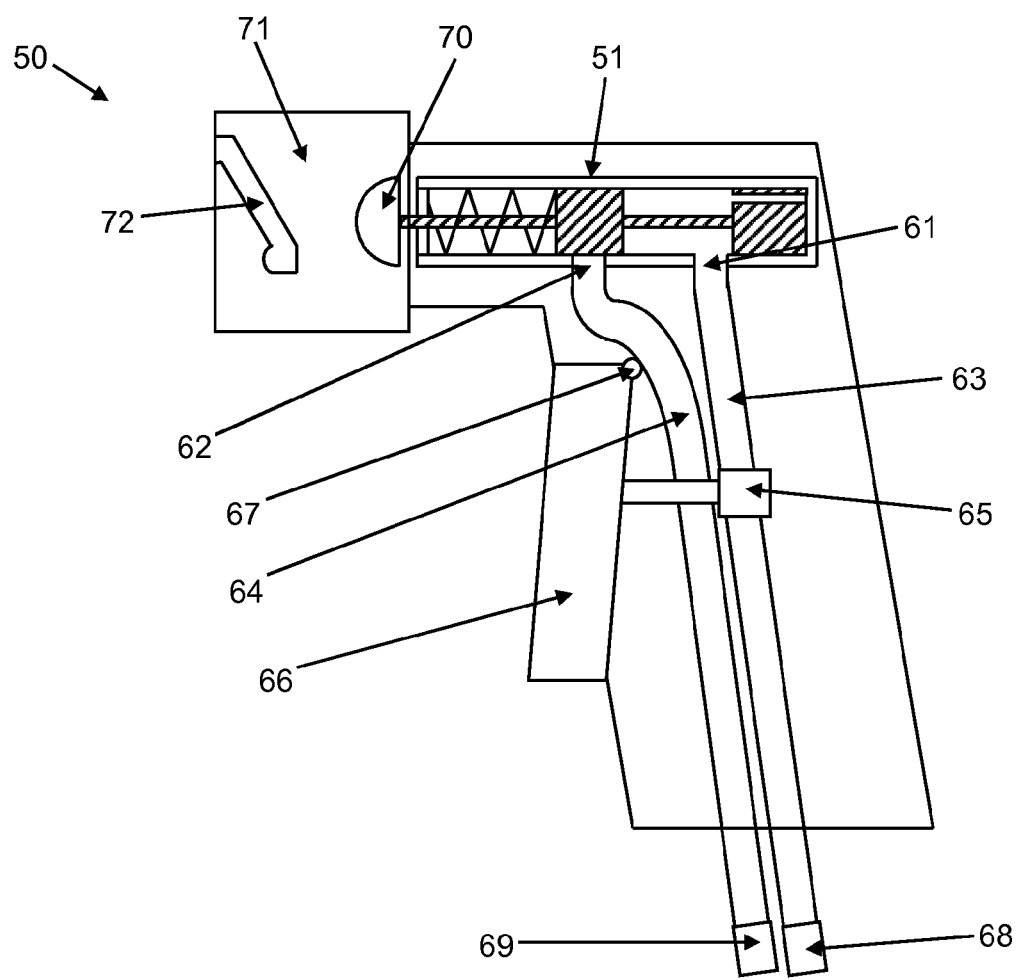
Figure 7:
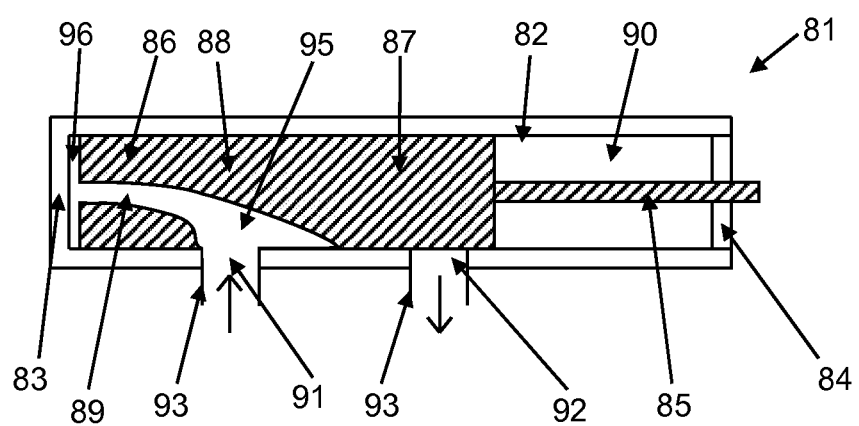

If the two plunger parts and the plunger rod and, if applicable, the connection have a low mass and thus low inertia, i.e. if the spring is dimensioned appropriately and the gas pressure is sufficient, high pulse rates and high frequencies can be attained with the device. The plunger rod can then transmit the pulses through a pestle to suitable membranes or other transmission facilities in order to attain pulses and therefore spray puffs containing a rinsing liquid.

It is also advantageous to arrange a third plunger part on the plunger rod, in place of the spring, as restoring facility which third plunger part is connected fixedly to the plunger rod and can also be connected fixedly to the second plunger part. The third plunger part can contain at least one axial gas-permeable bore hole. Moreover, a third opening is arranged in the hollow cylinder and is also connected to a reservoir containing a compressed gas, and a fourth opening connected to the surroundings is arranged in the hollow cylinder. In this variant, the driving process proceeds in alternating succession in the direction of the pestle and then in opposite direction for the restoring motion by means of the third plunger and the third and fourth openings.

The scope of the invention also includes attaching means for a lavage attachment to be arranged on the hollow cylinder. Specifically, a bayonet catch is particularly well-suited as attaching means.

A handle is also advantageous, whereby an operating lever is arranged in said handle that controls a valve that is connected to the compressed gas reservoir and to the first opening and, if applicable, to the third opening in gas-permeable manner. Moreover, the handle has a discharge opening for the relaxed gas provided in it.

The compressed gas motor can be operated through a stationary compressed gas facility or just as well through gas cartridges. A drive by means of carbon dioxide cartridges which are advantageous in that carbon dioxide is inexpensive to procure and is non-toxic is preferable in this context.

Exemplary embodiments of the invention shall be illustrated in the following on the basis of seven schematic figures, though without limiting the scope of the invention. In the figures:

FIG. 1: shows a schematic cross-sectional view of a compressed gas motor according to the invention with the pestle retracted;

FIG. 2: shows a schematic cross-sectional view of the compressed gas motor according to the invention according to FIG. 1 with the pestle driven out;

FIG. 3: shows a schematic cross-sectional view of a second compressed gas motor according to the invention with the pestle retracted;

FIG. 4: shows a schematic cross-sectional view of the compressed gas motor according to the invention according to FIG. 3 with the pestle in an intermediate position;

FIG. 5: shows a schematic cross-sectional view of the compressed gas motor according to the invention according to FIG. 3 with the pestle driven out;

FIG. 6: shows a schematic cross-sectional view of a lavage system according to the invention; and FIG. 7: shows a cross-sectional view of a third compressed gas motor according to the invention.

FIG. 1 shows a linear compressed gas motor 1 having a cylindrical housing that houses a cylindrical internal space 2 by means of internal walls. The first base surface 3 of the cylindrical internal space 2 (on the left side in FIG. 1) is closed in gas-tight and pressure-tight manner. The second base surface 4 of the cylindrical internal space is also closed, but comprises a passage for a plunger rod 5 that extends into the inside of the internal space 2.

The plunger rod 5 has two cylindrical plunger parts 6, 7 connected to it that are arranged on the inside of the internal space 2 such as to be shiftable, i.e. such as to be mobile in longitudinal direction of the cylindrical internal space 2. The two plunger parts 6, 7 are connected to each other through a connecting rod 8. The first plunger part 6 comprises a passage 9 in the form of a bore hole, whereas the second plunger part 7 has no passage. The two plunger parts 6, 7 end tightly against the internal wall of the internal space 2. A spring 10 is arranged between the second base surface 4 of the internal space 2 and the second plunger part 7 and presses the plunger 6, 7 with the plunger rod 5 and the connecting rod 8 in the direction of the first base surface 3.

The first plunger part 6 is positioned at the tightly closed first base surface 3. Said position of the system consisting of plunger 6, 7, connecting rod 8, and plunger rod 5, is defined as starting position since it is the position established through the pressure of the spring 10 without application of a pressure. Two openings 11, 12 are arranged in the cylinder jacket walls of the internal space 2 and have connectors 13 for attaching a tube or a hose (not shown) arranged on them. According to the invention, a compressed gas source is to be connected at the first opening 11, whereas the second opening 12 is simply open to the surroundings in the simplest of cases, but can just as well be connected to a discharge conduit.

For transmission of impacts, a pestle 14 is arranged on the end of the plunger rod 5 that projects from the compressed gas motor 1. The two plunger parts 6, 7 are positioned at a distance from each other by means of the connecting rod 8. Thus, an intermediate space 15 is formed between the plunger parts 6, 7 and moves along with the motion of the plunger parts 6, 7 in the internal space 2 of the compressed gas motor. An internal space region 16 is enclosed between the first plunger part 6 and the first base surface 3 and has no volume in FIG. 1 since the first plunger part 6 touches against the base surface 3 in the starting position shown in the figure.

If a positive pressure is applied at the first opening 11 while the compressed gas motor 1 is in the starting position shown in FIG. 1, the pressure acting on the first side of the second plunger part 7 facing the first plunger part 6 increases. This increases the force that is applied to said first side of the second plunger part 7. The ambient atmospheric pressure acting on the pestle 14 and the second side of the plunger part 7 facing the spring 10 acts as a counter-force. In addition, the spring 10 exerts a force on said second side. If a force applied through compressed air or another compressed gas onto the first side of the plunger part 7 overcomes the forces acting on the second side of the plunger part and the frictional force, this will lead to a motion of the plunger system comprising the plunger parts 6, 7, the connecting rod 8, the plunger rod 5 (areas shown hatched in FIG. 1), and the pestle 14 away from the first base surface 3 of the internal space 2. In the process, the spring 10 is being compressed which, in turn, increases the force acting against the motion during the motion. If the second base surface 4 of the internal space 2 is also closed in gas-tight manner through providing a gas-tight feed-through for the plunger rod 5, the air enclosed in said part of the internal space 2, which is enclosed through the second side of the second plunger part 7 and through the second base surface 4, and/or the enclosed gas effect(s) a force that is inverse proportional to the volume of said part of the internal space 2 and is directed against the motion of the plunger.

The compressed air or the compressed gas penetrates through the passage 9 [into the space] between the first side (on the left side in FIG. 1) of the first plunger part 6 and the end of the first base surface 3. This increases the volume in the internal space 2 for the compressed gas supplied through the first opening 11. The motion will proceed to the second opening 12 to the outlet, which is covered through the second plunger part 7 in the starting position, being opened and the compressed gas escaping through the opening 12 from the intermediate space 15 and the space between the first plunger part 6 and the first base surface 3. Due to the inertia of the motion of the plunger system and the flow resistances acting on the escaping compressed gas, the motion is not arrested instantaneously, though, but continues up to a second position at which the motion is reversed. Where exactly the second position is situated depends on various parameters, such as the exact geometry of the structure, the friction of plunger parts 6, 7 at the internal walls of the internal space 2, the spring constants of the spring 10, the gas pressure at the first opening 11, the flow resistances downstream of the second opening 12, and the ambient atmospheric pressure. The motion of the plunger system 5, 6, 7, 8 ends at the second base surface 4 at the latest.

FIG. 2 shows the second position at which the motion of plunger system 5, 6, 7, 8 is reversed. The first plunger part 6 closes the first opening 11. The compressed gas also escapes from the internal space region 16 between the first plunger part 6 and the first base surface 3 through the passage 9 (indicated by the horizontal arrow like in FIG. 2) and ultimately from the second opening 12, which is not closed through the second plunger part 7 in this position. Thus, the pressure acting on the first, left side of the second plunger part 7 decreases. Ultimately, the counter-forces due to the spring 10 lead to the motion being reverted and the plunger system 5, 6, 7, 8 being accelerated in the direction of the first base surface 3. The spring force decreases due to the motion in the direction of the first base surface 3. Concurrently, the second opening 12 is closed through the second plunger part 7 and the first opening 11 is re-opened such that a pressure can build-up again in the intermediate space 15 and in the internal space region 16 between the first plunger part 6 and the first base surface 3 of the internal space. The plunger system 5, 6, 7, 8 returns to the starting position according to FIG. 1 and the motion starts anew.

As long as a compressed gas is applied at the first opening 11 and is supplied cyclically in this manner and the second opening 12 remains open to a normal pressure region or negative pressure region, the motion continues cyclically. The resulting motion of the pestle 14 can be utilised to generate spray puffs of a rinsing liquid, for example in that the pestle 14 hits against a membrane that passes the pressure impact to the rinsing liquid positioned behind it which can then exit through one or more nozzles.

FIGS. 3, 4, and 5 show schematic cross-sectional views of an alternative compressed gas motor 21, in which an additional plunger drive is used as restoring facility rather than a spring like in the preceding exemplary embodiment.

A cylindrical internal space 22 of the compressed gas motor 21 is closed at a first base surface 23 and a second base surface 24 in gas-tight manner. A plunger rod 25 projects from the internal space 22 through a gas-tight opening in the second base surface 24. The plunger rod 25 is arranged in the direction of the cylinder axis of the internal space 22 such as to be mobile through the second base surface 24.

Three plunger parts 26, 27, 38 are arranged at the plunger rod 25. The first plunger part 26 is arranged at the end of the plunger system 25, 26, 27, 28, 28', 38 that is opposite from the second base surface 24. The second plunger part 27 is connected to the first plunger part 26 by means of a connecting rod 28 such that it is situated at a distance from the first plunger part 26. A passage 29 in the form of a bore hole is arranged in the first plunger part 26.

A first opening 31 and a fourth opening 31' for supplying a compressed gas as well as a second opening 32 and a third opening 32' for discharging a gas are arranged in the cylinder jacket wall of the internal space 22. Connectors 33 for connecting a tube or hose are arranged at the openings 31, 31', 32, 32'.

A pestle 34 in the shape of a mushroom is secured to the end of the plunger rod 25 that projects through the second base surface 24 out of the compressed gas motor 21. Upon an oscillating motion of the plunger system 25, 26, 27, 28, 28', 38 in the internal space 22, the pestle 34, at the fully driven-out position shown in FIG. 5, serves to exert an impact on a liquid reservoir in order to generate spray puffs for a lavage system.

The distance between the first plunger part 26 and the second plunger part 27 leads to a first intermediate space 35 being formed in the internal space 22. A first internal space region 36 is formed between the first plunger part 26 and the first base surface 23 and has no volume in FIG. 3 and opens up in other positions of the plunger system 25, 26, 27, 28, 28', 38 according to FIGS. 4 and 5. Another intermediate space 37 is arranged between the second plunger part 27 and a third plunger part 38. The third plunger part 38 comprises a passage 39 and is basically structured like the first plunger part 26. The third plunger part 38 is connected to the second plunger part 27 by means of a connecting rod 28'. A second internal space region 40 is formed between the third plunger part 38 and the closed second base surface 24 and has a maximal volume in the starting position (FIG. 3) of the plunger system 25, 26, 27, 28, 28', 38, whereas it has no volume any more in the final position (FIG. 5). Unlike the variable volumes of the two internal space regions 36, 40, the intermediate spaces 35, 37 have fixed predetermined volumes inside the internal space 22.

The first plunger part 26, the second plunger part 27, the third plunger part 38, and the connecting rods 28, 28' form a plunger 26, 27, 28, 28', 38 that is mobile in the direction of the cylinder axis on the inside of the cylindrical internal space 22. The second intermediate space 37, the third plunger part 38 with the passage 39, the second internal space region 40, and the second base surface 24, which is closed such as to be gas-tight, join the third opening 32' and the fourth opening 31' in this embodiment to form a restoring facility for the plunger system 25, 26, 27, 28, 28', 38.

The plunger parts 26, 27, 38 end tightly against the cylinder jacket walls of the internal space 22 and are guided therein. Depending on the position of the plunger 26, 27, 28, 28', 38, the first plunger part 26 can cover or leave open the first opening 31 for supplying a compressed gas, the third plunger part 38 can cover or leave open the fourth opening 31' for supplying a compressed gas, and the second plunger part 27 can cover the second opening 32 and the third opening 32' for discharging the gas or leave either one of them open. Only one of the two inlet openings 31, 31' and one of the two outlet openings 32, 32' can be open at any time. When the first opening 31 for supplying a compressed gas is open, the second opening 32 for discharging the gas, which is expanded by then, is closed. The same applies to the two other openings 31' and 32'. The plunger part 27 renders a first gas plunger chamber 29, 35, 36 and a second gas plunger chamber 37, 39, 40 separated from each other and these thus form separate gas plunger chambers, or motor parts, as it may be, by means of the passages 29 and 39.

In the starting position shown in FIG. 3, a compressed gas flows through the opening 31 into the first intermediate space 35 and into the first passage 29 of the first plunger part 26. There, the gas presses onto the first base surface 23. Concurrently, a gas escapes from the second intermediate space 37 and, through the passage 39 of the third plunger part 38, also from the second internal space region 40 through the third opening 32'. Since the pressure in the first gas plunger chamber 29, 35, 36 becomes larger than the pressure in the second gas plunger chamber 37, 39, 40, the plunger 26, 27, 28, 28', 38 is moved in the direction of the second base surface 24 such that the plunger rod 25 is driven out of the internal space 22 of the compressed gas motor 21.

The motion of the first plunger part 26 closes the first opening 31 and then, upon further motion of the plunger 26, 27, 28, 28', 38, the second opening 32 is opened. This leads to the pressure in the first gas plunger chamber 29, 35, 36 decreasing. Concurrently, the third opening 32' is closed through the second plunger part 27, upon which the reduction of the volume of the second internal space region 40 causes a pressure to build-up in the second gas plunger chamber 37, 39, 40. This situation is shown in FIG. 4. However, since it takes some time for the pressure in the first gas plunger chamber 29, 35, 36 to be released and due to the inertia of the plunger system 25, 26, 27, 28, 28', 38 including pestle 34, the plunger 26, 27, 28, 28', 38 continues its motion to the position shown in FIG. 5. The motion of the plunger 26, 27, 28, 28', 38 ends at the second base surface 24 and the fourth opening 31' opens while the second opening 32 is still wide open. Thus, the compressed gas flows through the fourth opening into the second gas plunger chamber 37, 39, 40 where it builds up a pressure, while the expanded gas escapes from the first gas plunger chamber 29, 35, 36 through the second opening 32. In that a pressure difference with reversed sign is being built-up in the two gas plunger chambers 29, 35, 36 and 37, 39, 40, the plunger 26, 27, 28, 28', 38 is now being accelerated in the direction of the first base surface 23.

The plunger returns beyond the position shown in FIG. 4 to the starting position according to FIG. 3. Due to the inertia of the plunger 26, 27, 28, 28', 38 in the reversed motion and the pressure difference being reduced only slowly, the plunger 26, 27, 28, 28', 38 returns to the starting position. The motion of the plunger 26, 27, 28, 28', 38 then continues in new cycles.

FIG. 6 shows a cross-sectional view of the schematic structure of a handle 50 according to the invention for a lavage system. A compressed gas motor 51 according to the invention is arranged in said handle 50. The compressed gas motor comprises a first opening 61 for supplying compressed air and a second opening 62 for gas discharge. The two openings 61, 62 are connected to a compressed air conduit 63 and a discharge conduit 64.

A valve 65 is arranged in the compressed air conduit 63. The valve 65 can be operated manually by means of an operating facility in the form of an operating lever 66 that is connected to the handle 50 by means of a hinge 67 such that it can rotate. The compressed air conduit 63 comprises a connector 68 by means of which it can be connected to a compressed air source. The discharge conduit 64 ends in the surroundings or is connected through a second connector 69 to a exhaust air system or even a vacuum pump for generating a negative pressure.

A bracket 71 having a bayonet catch 72 for a lavage system (not shown) is arranged in the region of the pestle 70 that is attached on the compressed gas motor 51. A lavage system can be connected to the handle 50 by means of the bracket 71 and the bayonet catch 72. Actuating the operating lever 66 enables a user to operate the valve 65 and thus supply compressed air via the compressed air conduit 63 to the compressed gas motor 51. This causes the compressed gas motor 51 to move such that the pestle 70 hits at high frequency against a liquid reservoir of the lavage system. This causes spray puffs to be generated at high frequency that can be used to clean tissues areas of a patient.

FIG. 7 shows a schematic cross-sectional view of a third embodiment of a compressed gas motor 81 according to the invention. A cylindrical internal space 82 is closed in gas-tight manner at both base surfaces 83, 84. The second base surface 84 comprises an opening for a plunger rod 85. The plunger rod 85 is secured in fixed and immobile manner to a plunger 86, 87, 88 formed through a first plunger part 86, a second plunger part 87, and a connection 88. The plunger 86, 87, 88 and the plunger rod 85 are mobile in longitudinal direction of the internal space 82.

A passage 89 is arranged in the first plunger part 86. Since the plunger 86, 87, 88 closes tightly against the internal walls of the internal space 82, the region of the internal space 22 that is being closed by means of the second plunger part 87 and the second base surface in gas-tight manner, is a gas spring 90. The gas spring 90 acts as a restoring facility for the compressed gas motor 81.

The cylinder jacket of the internal space 82 has a first opening 91 for supplying a compressed gas and a second opening 92 for discharging a gas provided in it. Connectors 93 for connecting conduits are arranged at the openings. In the region of the connection 88, the plunger 86, 87, 88 forms an intermediate space 95 between the first plunger part 86 and the second plunger part 87. An internal space region 96, whose volume depends on the position of the plunger 86, 87, 88 in the internal space 82 of the compressed gas motor 81, is formed between the first plunger part 86 and the first base surface 83.

The pressure in the gas spring 90 must be selected appropriately such that it is less than the pressure of the compressed gas supplied through the first opening 91. Preferably, the pressure in the gas spring 90 is selected to be higher than the ambient pressure. The periodical motion of the compressed gas motor 81 proceeds according to the pattern shown in the first exemplary embodiment according to FIGS. 1 and 2.

The features of the invention disclosed in the preceding description and in the claims, figures, and exemplary embodiments, can be essential for the implementation of the various embodiments of the invention both alone and in any combination.

LIST OF REFERENCE NUMBERS 1, 21, 51, 81 Compressed gas motor
2, 22, 82 Internal space
3, 23, 83 First base surface
4, 24, 84 Second base surface
5, 25, 85 Plunger rod
6, 26, 86 First plunger part
7, 27, 87 Second plunger part
8, 28, 28' Connecting rod
9, 29, 39, 89 Passage/bore hole
10, 90 Spring
11, 31, 61, 91 First opening
12, 32, 62, 92 Second opening
13, 33, 93 Connecting piece/sleeve
14, 34, 70 Pestle
15, 35, 37, 95 Intermediate space
16, 36, 40, 96 Internal space region
31' Fourth opening
32' Third opening
38 Third plunger part
50 Handle
63 Compressed air conduit
64 Exhaust air conduit
65 Valve
66 Operating lever
67 Hinge
68, 69 Connector
71 Bracket
72 Bayonet catch
88 Connection

The invention claimed is:

1. A compressed gas motor, for operating a lavage system, comprising
- a cylindrical internal space closable in gas-tight manner at least at one first base surface;
- at least one plunger arranged in the cylindrical internal space such as to be mobile along the cylinder axis and ending tightly against the cylindrical internal space;
- a plunger rod connected to the at least one plunger and projecting from the cylindrical internal space beyond a second base surface;
- a first opening for supplying a compressed gas into the cylindrical internal space; and
- a second opening for discharging a gas from the inside of the cylindrical internal space; wherein
the first and second openings are arranged in a cylinder jacket of the cylindrical internal space,
whereby the first opening is arranged between the second opening and the closed first base surface; wherein
the plunger comprises a first plunger part and a second plunger part that are connected to each other;

whereby the first plunger part comprises at least one passage and/or forms at least one passage between the first plunger part and the cylinder wall of the cylindrical internal space; and the second plunger part closes the inside of the cylindrical internal space such as to be tight, whereby at least one passage of the first plunger part connects an intermediate space between the first and the second plunger part to an internal space region between the closed first base surface and the first plunger part; and whereby the first opening is closable through the first plunger part and the second opening is closable through the second plunger part; and the compressed gas motor comprises a restoring facility that exerts, at least for part of the time, a force on the plunger in a direction of the first base surface of the cylindrical internal space when the second plunger part does not close the second opening completely.

2. The compressed gas motor according to claim 1, wherein the wall of the cylindrical internal space comprises a groove extending from the region of the end of the first base surface of the cylindrical internal space to the region of the height of the second opening and forming at least one passage between the first plunger part and the cylinder wall of the cylindrical internal space, whereby the groove is not connected to the openings.

3. The compressed gas motor according to claim 2, wherein the groove extends up to the end of the first base surface of the cylindrical internal space (2, 22, 82) and in that the first plunger part is a cylindrical body comprising no further passages.

4. The compressed gas motor according to claim 1, wherein the first plunger part and the second plunger part are connected to each other by means of a rigid connection, by means of a rod.

5. The compressed gas motor according to claim 1, wherein the second base surface of the cylindrical internal space is open.

6. The compressed gas motor according to claim 1, wherein a bracket for the plunger rod is arranged on the second base surface of the cylindrical internal space and supports the plunger rod centric in a region of the cylinder axis of the cylindrical internal space.

7. The compressed gas motor according to claim 1, wherein the at least one passage comprises a patent, gas-permeable bore hole in the first plunger part.

8. The compressed gas motor according to claim 1, wherein a distance between the first plunger part and the second plunger part is between 1 mm and 100 mm.

9. The compressed gas motor according to claim 1, wherein a distance of the first opening from the closed first base surface is at least equal to a height of the first plunger part in a direction of the cylinder axis of the cylindrical internal space.

10. The compressed gas motor according to claim 1, wherein the first plunger part or the second plunger part are cylindrical, at least regions thereof, and contact the internal wall of the cylindrical internal space.

11. The compressed gas motor according to claim 1, wherein a reservoir is connected at the first opening and contains compressed gas or the second opening is connected to surroundings of the compressed gas motor in gas-permeable manner, without any conduits impeding the gas flow.

12. The compressed gas motor according to claim 1, wherein attaching means for attachment of a lavage attachment are arranged on an outside in a region of the second base surface.

13. The compressed gas motor according to claim 1, wherein an end of the plunger rod projecting from the second base surface comprises a pestle.

14. The compressed gas motor according to claim 1, wherein the plunger parts, the connections of the plunger parts, the plunger rod, the walls of the cylindrical internal space, the end(s) of the base surfaces, the bracket, the restoring facility, the attaching means and/or the pestle are made of plastic material, and are injection molding components.

15. The compressed gas motor according to claim 1, wherein the cylindrical internal space is an inside of a cylindrical tube and the compressed gas motor comprises, at least in regions thereof, a cylindrical external surface.

16. The compressed gas motor according to claim 1, wherein the first opening and the second opening are closable completely through the first plunger part and the second plunger part, respectively, in alternating manner, during an oscillating motion of the plunger in the cylindrical internal space.

17. The compressed gas motor according to claim 1, wherein the restoring facility comprises a spring arranged between the second plunger part and the second base surface of the cylindrical internal space.

18. The compressed gas motor according to claim 1, wherein the restoring facility comprises a third plunger part;
   a third opening for discharge of gas from the inside of the internal space; and
   a fourth opening for supplying compressed gas into the internal space;
   whereby the third and fourth openings are arranged in the cylinder jacket of the cylindrical internal space;
   the fourth opening is arranged between the second opening and the second base surface of the cylindrical internal space;
   the third opening is arranged between the second opening and the fourth opening;
   the third opening and the fourth opening are closable through the second plunger part and the third plunger part, respectively;
   and whereby the third plunger part is a part of the plunger that is arranged on the plunger rod between the second plunger part and the second base surface of the cylindrical internal space and is connected to the second plunger part; and
   the third plunger part comprises at least one passage or forms at least one passage between the third plunger part and the cylinder wall of the internal space.

19. The compressed gas motor according to claim 18, wherein the third plunger part is structured like the first plunger part the internal wall of the cylindrical internal space is structured with respect to the third plunger part like it is structured with respect to the first plunger part.

20. The compressed gas motor according to claim 1, wherein the plunger rod is connected to the plunger such as to be rigid and immobile, and is connected to the second plunger part or the third plunger part, in particular in the region of the cylinder axis.

21. A handle for a lavage system comprising the compressed gas motor according to claim 1, the lavage system comprises a valve and an operating facility for controlling the valve that is arranged on the handle, whereby the valve is arranged in a conduit that is connected to the first opening or second opening.

22. A lavage system comprising the compressed gas motor according to claim 1, the lavage system comprises a handle and a rinsing liquid reservoir or a connector for a rinsing liquid reservoir, whereby impacts of force can be transmitted by means of the end of the plunger rod that projects beyond the second base surface to a force transmission facility in order to generate spray puffs containing the rinsing liquid.

23. A method, for operating the compressed gas motor according to claim 1, comprising:
- supplying a compressed gas through the first opening into an intermediate space between the first and second plunger part;
- building-up a positive pressure in the intermediate space;
- motioning, due to the positive pressure, the plunger parts in the internal space of the compressed gas motor;
- closing the first opening and opening the second opening through the motion of the plunger parts;
- releasing the expanded gas through the second opening from the intermediate space;
- restoring the plunger parts in the internal space through a restoring facility.

* * * * *